(12) United States Patent
Lyden et al.

(10) Patent No.: US 8,391,992 B2
(45) Date of Patent: Mar. 5, 2013

(54) IMPLANTABLE MEDICAL DEVICE SWITCHING POWER SUPPLY INCLUDING MULTIPLE MODES

(75) Inventors: Michael J. Lyden, Shoreview, MN (US); Nicholas J. Stessman, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 219 days.

(21) Appl. No.: 12/956,375

(22) Filed: Nov. 30, 2010

(65) Prior Publication Data

US 2011/0160806 A1 Jun. 30, 2011

Related U.S. Application Data

(60) Provisional application No. 61/291,243, filed on Dec. 30, 2009.

(51) Int. Cl.
*A61N 1/00* (2006.01)
(52) U.S. Cl. .......................................................... 607/63
(58) Field of Classification Search .................... 607/63, 607/9; 363/98; 604/500; 324/253
See application file for complete search history.

(56) References Cited

U.S. PATENT DOCUMENTS

| | | | |
|---|---|---|---|
| 5,287,059 A | 2/1994 | Ando et al. | |
| 5,545,187 A | 8/1996 | Bergstrom et al. | |
| 5,552,979 A * | 9/1996 | Gu et al. | 363/98 |
| 5,662,694 A | 9/1997 | Lidman et al. | |
| 7,050,855 B2 | 5/2006 | Zeijlemaker et al. | |
| 7,082,328 B2 * | 7/2006 | Funke | 607/9 |
| 7,242,981 B2 | 7/2007 | Ginggen | |
| 7,369,898 B1 | 5/2008 | Kroll et al. | |
| 7,509,167 B2 | 3/2009 | Stessman | |
| 7,561,915 B1 | 7/2009 | Cooke et al. | |
| 7,623,930 B2 | 11/2009 | Zeijlemaker et al. | |
| 7,672,726 B2 | 3/2010 | Ginggen | |
| 2003/0144705 A1 | 7/2003 | Funke | |
| 2004/0052392 A1 | 3/2004 | Sacha et al. | |
| 2004/0267233 A1 * | 12/2004 | Ginggen | 604/500 |
| 2006/0167496 A1 | 7/2006 | Nelson et al. | |
| 2006/0293591 A1 | 12/2006 | Wahlstrand et al. | |
| 2007/0191914 A1 | 8/2007 | Stessman | |
| 2009/0182389 A1 | 7/2009 | Stessman | |

FOREIGN PATENT DOCUMENTS

| | | |
|---|---|---|
| EP | 0670170 A1 | 9/1995 |
| EP | 0718010 A1 | 6/1996 |
| JP | 04-024574 | 1/1992 |
| JP | 08-047543 | 2/1996 |
| JP | 08-215323 | 8/1996 |

(Continued)

OTHER PUBLICATIONS

"U.S. Appl. No. 11/276,159, Final Office Action mailed Aug. 20, 2008", 5 pgs.

(Continued)

*Primary Examiner* — George Manuel
*Assistant Examiner* — Robert N Wieland
(74) *Attorney, Agent, or Firm* — Schwegman Lundberg & Woessner, P.A.

(57) ABSTRACT

An implantable or other ambulatory medical device can include a magnetic field detector, such as configured to detect an intense magnetic field. In an example, the ambulatory or implantable medical device can include an inductive switching supply, such as including one or more of a peak current comparator, or a zero current comparator. In an example, the ambulatory or implantable medical device can include a controller circuit, configured to control a switch, such as to controllably charge an inductor included in the inductive switching supply.

20 Claims, 7 Drawing Sheets

FOREIGN PATENT DOCUMENTS

| | | |
|---|---|---|
| JP | 200521688 A | 1/2005 |
| JP | 2005515857 | 6/2005 |
| WO | WO-03063962 A1 | 8/2003 |
| WO | WO-2005035048 A2 | 4/2005 |
| WO | WO-2005035048 A3 | 4/2005 |
| WO | WO-2006081434 A1 | 8/2006 |
| WO | WO-2007094976 A1 | 8/2007 |

OTHER PUBLICATIONS

"U.S. Appl. No. 11/276,159, Non-Final Office Action mailed Oct. 26, 2007", 6 pgs.

"U.S. Appl. No. 11/276,159, Notice of Allowance mailed Nov. 14, 2008", 4 pgs.

"U.S. Appl. No. 11/276,159, Response filed Feb. 26, 2008 to Non-Final Office Action mailed Oct. 26, 2007", 9 pgs.

"U.S. Appl. No. 11/276,159, Response filed Oct. 20, 2008 to Final Office Action mailed Aug. 20, 2008", 9 pgs.

"U.S. Appl. No. 12/409,766, Non-Final Office Action mailed Sep. 16, 2010", 7 pgs.

"European Application Serial No. 0774978.6, Office Action mailed Sep. 23, 2008", 2 pgs.

"European Application Serial No. 0774978.6, Response filed Oct. 22, 2008 to Office Action mailed Sep. 23, 2008", 16 pgs.

"European Application Serial No. 07749781.6, Office Action mailed Nov. 22, 2010", 4 pgs.

"International Application Serial No. PCT/US2007/002848, International Search Report mailed Jun. 19, 2007", 5 pgs.

"International Application Serial No. PCT/US2007/002848, Written Opinion mailed Jun. 19, 2007", 8 pgs.

"U.S. Appl. No. 12/409,766, Final Office Action mailed Mar. 14, 2011", 6 pgs.

"U.S. Appl. No. 12/409,766, Notice of Allowance mailed May 8, 2012", 7 pgs.

"U.S. Appl. No. 12/409,766, Notice of Allowance mailed Aug. 15, 2012", 7 pgs.

"U.S. Appl. No. 12/409,766, Notice of Allowance mailed Dec. 28, 2011", 8 pgs.

"U.S. Appl. No. 12/409,766, Response filed Dec. 16, 2010 to Non Final Office Action mailed Sep. 16, 2010", 10 pgs.

"U.S. Appl. No. 12/409,766, Response filed Jun. 14, 2011 to Final Office Action mailed Mar. 14, 2011", 8 pgs.

"European Application Serial No. 07749781.6, Response filed May 5, 2011 to Non Final Office Action mailed Nov. 22, 2010", 12.

"Japanese Application Serial No. 2008-555259, Office Action mailed Dec. 20, 2011", W/ English Translation, 8 pgs.

"Japanese Application Serial No. 2008-555259, Response filed Apr. 16, 2012 to Office Action mailed Dec. 20, 2011", (w/ English Translation of Amended Claims), 10 pgs.

* cited by examiner

IMPLANTABLE MEDICAL DEVICE SWITCHING POWER SUPPLY INCLUDING MULTIPLE MODES

CLAIM OF PRIORITY

This patent application claims the benefit of priority, under 35 U.S.C. Section 119(e), to Lyden, et al., U.S. Provisional Patent Application Ser. No. 61/291,243, entitled "Implantable Medical Device Switching Power Supply Including Multiple Modes," filed on Dec. 30, 2009, which is hereby incorporated by reference herein in its entirety.

BACKGROUND

Implantable medical devices (IMDs) can perform a variety of diagnostic or therapeutic functions. In an example, an IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), cardiac resynchronization therapy (CRT) devices, implantable monitors, neuromodulation devices (e.g., deep brain stimulators, or other neural stimulators), cochlear implants, or drug pumps, among others.

Nuclear magnetic resonance imaging (MRI) is a medical imaging technique that can be used to visualize internal structure of the body. MRI is an increasingly common diagnostic tool, but can pose risks to a person with an IMD, such as a patient undergoing an MRI scan or a person nearby MRI equipment, or to people having a conductive implant.

In an MR field, an item, such as an IMD, can be referred to as "MR Safe" if the item poses no known hazard in all MRI environments. In an example, MR Safe items can include non-conducting, non-metallic, non-magnetic materials, such as glass, porcelain, a non-conductive polymer, etc. An item can be referred to as "MR Conditional" in the MR field if the item has been demonstrated to pose no known hazards in a specified MRI environment with specified conditions of use (e.g., static magnetic field strength, spatial gradient, time-varying magnetic fields, RF fields, etc.). In certain examples, MR Conditional items can be labeled with testing results sufficient to characterize item behavior in a specified MRI environment. Testing can include, among other things, magnetically induced displacement or torque, heating, induced current or voltage, or one or more other factors. An item known to pose hazards in all MRI environments, such as a ferromagnetic scissors, can be referred to as "MR Unsafe."

Overview

Ambulatory or implantable medical devices (IMDs), such as cardiac function management device, can include an "MRI mode," such as activated manually or automatically. The MRI mode can configure the device into an "MR Conditional" mode, such as including a non-sensing, fixed-rate pacing mode such as to maintain pacing therapy during an MRI scan. In an example, high-voltage tachyarrhythmia therapy (e.g., defibrillation shock) can be disabled in the MRI mode, such as to prevent inappropriate shocks from being administered by the device, with the patient being closely monitored during the MRI procedure, or to prevent unwanted torques or forces being exerted on the IMD or one or more other conductive implants (e.g., a lead or sensor subsystem, separate from or attached to the IMD, etc.).

In an example, the MRI mode may mitigate some of the hazards to a subject in or near an MR fields, such as generated by nuclear magnetic resonance (NMR) equipment (e.g., an NMR spectrometer, an MRI scanner, etc.). However, if the MRI mode is not configured automatically, this mitigation can need the intervention of an external programmer and an electrophysiologist, cardiologist, or likewise skilled medical professional capable of temporarily re-programming the device into the MRI mode. At the end of the MRI scan, the medical professional can then restore the device to its previous mode of operation, such as before the patient can be released. The present inventors have recognized, among other things, that burden of performing an MRI procedure on a subject having an IMD can be reduced if the IMD can detect nearby NMR equipment, automatically activating MRI mode when necessary.

In an example, an IMD can include one or more power supplies, such as one or more relatively high-efficiency switching power supplies. The present inventors have also recognized, among other things, that the operation of an inductive switching supply can be altered by the presence of externally-applied electromagnetic fields, such as one or more of a static, spatial gradient, or RF excitation field, such as used by NMR equipment (e.g., an MRI scanner or an NMR spectrometer, or other NMR device). In an example, the IMD can include an inductive switching power supply having more than one mode, such as a non-MRI mode and an MRI-mode. In the non-MRI mode, the switching supply can use an inductor with an unsaturated ferrite core. In the MRI mode, the switching supply can use an inductor having a saturated core or having a reduced inductance, such as by adjusting one or more power supply operating parameters including one or more of a comparator bias, a peak or minimum inductor current, or a duration of one or more of a charge phase or dump phase of operation.

An implantable or other ambulatory medical device can include a magnetic field detector, such as configured to detect an intense magnetic field. In an example, the ambulatory or implantable medical device can include an inductive switching supply, such as including one or more of a peak current comparator, or a zero current comparator. In an example, the ambulatory or implantable medical device can include a controller circuit, configured to control a switch, such as to controllably charge an inductor included in the inductive switching supply.

Example 1 includes subject matter (such as an apparatus) comprising an implantable medical device, including a magnetic field detector, an inductive switching supply including an inductor having a ferromagnetic core, a peak current comparator configured to compare an inductor current through the inductor to a specified peak current threshold, and a zero current comparator configured to compare the inductor current to a specified minimum inductor current threshold, a controller circuit configured to control a state of a switch using information from the peak current comparator and the zero current comparator when the implantable medical device is configured in a first mode of operation. In Example 1, the switch can be configured to controllably charge the inductor, and the controller circuit can be configured to adjust the implantable medical device to the first mode of operation in response to information provided by the magnetic field detector indicating an absence of an intense magnetic field.

In Example 2, the subject matter of Example 1 can optionally include a magnetic field detector comprising a Hall effect sensor.

In Example 3, the subject matter of one or any combination of Examples 1-2 can optionally include a magnetic field detector comprising a core saturation detector configured to detect saturation of the inductor, and the intense magnetic field, when present, is intense enough to saturate the inductor.

In Example 4, the subject matter of one or any combination of Examples 1-3 can optionally include a controller circuit configured to adjust the implantable medical device to a second mode of operation in response to information provided by the magnetic field detector indicating a presence of the intense magnetic field.

In Example 5, the subject matter of one or any combination of Examples 1-4 can optionally include a controller circuit comprising at least one timer circuit, the controller circuit configured to control the state of the switch using at least one of a specified maximum charge phase duration, or a specified maximum dump phase duration, using the timer circuit, when the implantable medical device is configured in the second mode of operation.

In Example 6, the subject matter of one or any combination of Examples 1-5 can optionally include, in the second mode of operation, one or more of the specified maximum charge duration or the specified maximum dump phase duration made shorter than a corresponding charge phase duration or dump phase duration in the first mode operation.

In Example 7, the subject matter of one or any combination of Examples 1-6 can optionally include an error comparator configured to compare an output of the inductive switching supply to a specified output reference, and configured to provide an error signal indicative of the comparison, and a controller circuit configured to adjust one or more of the charge phase duration, or the dump phase duration, using information about the error signal, when the implantable medical device is configured in the second mode of operation.

In Example 8, the subject matter of one or any combination of Examples 1-7 can optionally include an error comparator configured to compare an output of the inductive switching supply to a specified output reference, and configured to provide an error signal indicative of the comparison, and a controller circuit configured to adjust a repetition rate of successive charge and dump phases using information about the error signal, when the implantable medical device is configured in the second mode of operation.

In Example 9, the subject matter of one or any combination of Examples 1-8 can optionally include a controller circuit configured to adjust the implantable medical device back to the first mode of operation using information about the magnetic field provided by the magnetic field detector when the magnetic field detector is no longer exposed to an intense magnetic field.

In Example 10, the subject matter of one or any combination of Examples 1-9 can optionally include at least one of the peak current comparator or the zero current comparator comprising a first bias circuit used when the implantable medical device is in the first mode of a operation, and a second bias circuit used when the implantable medical device is in a second mode of operation, the second bias circuit configured to reduce a latency of at least one of the peak current comparator or the zero current comparator in the second mode of operation, as compared to the first mode of operation.

Example 11 includes subject matter (such as an apparatus) comprising an implantable medical device, including a magnetic field detector, an inductive switching supply including an inductor including a ferromagnetic core, a peak current comparator configured to compare an inductor current through the inductor to a specified peak current threshold, a zero current comparator configured to compare the inductor current to a specified minimum inductor current threshold, a controller circuit configured to control a state of a switch using information from the peak current comparator and the zero current comparator when the implantable medical device is configured in a first mode of operation. In Example 1, the switch can be configured to controllably charge the inductor, at least one of the peak current comparator or the zero current comparator includes a first bias circuit used when the implantable medical device is in the first mode of a operation, and a second bias circuit used when the implantable medical device is in the second mode of operation, the second bias circuit can be configured to reduce a latency of at least one of the peak current comparator or the zero current comparator in the second mode of operation, as compared to the first mode of operation, and the controller circuit can be configured to adjust the implantable medical device to the second mode of operation using information about a magnetic field provided by the magnetic field detector when the magnetic field detector is exposed to an intense magnetic field.

Example 12 can include, or can optionally be combined with the subject matter of one or any combination of Examples 1-11 to include, subject matter (such as a method, a means for performing acts, or a machine-readable medium including instructions that, when performed by the machine, cause the machine to perform acts) comprising detecting a magnetic field using an implantable medical device, the implantable medical device including an inductive switching supply. In Example 12, in response to detecting the magnetic field, this example can include adjusting the implantable medical device to a first mode of operation when information about a detected magnetic field indicates an absence of an intense magnetic field, and controllably charging an inductor included as a portion of the inductive switching supply via controlling a state of a switch, in the first mode of operation, the controlling the state of the switch including using information provided by comparing an inductor current to a specified peak current threshold; and comparing the inductor current to a specified minimum inductor current threshold.

In Example 13, the subject matter of Example 12 can optionally include detecting the magnetic field including detecting saturation of the inductor, and the intense magnetic field, when present, is intense enough to saturate the inductor.

In Example 14, the subject matter of one or any combination of Examples 12-13 can optionally include adjusting the implantable medical device to a second mode of operation when information about the detected magnetic field indicates a presence of an intense magnetic field.

In Example 15, the subject matter of one or any combination of Examples 12-14 can optionally include controlling the state of the switch, in the second mode of operation, using at least one of a specified maximum charge phase duration, or a specified maximum dump phase duration.

In Example 16, the subject matter of one or any combination of Examples 12-15 can optionally include, in the second mode of operation, one or more of the specified maximum charge duration or the specified maximum dump phase duration made shorter than a corresponding charge phase duration or dump phase duration in the first mode operation.

In Example 17, the subject matter of one or any combination of Examples 12-16 can optionally include controlling the state of the switch, in the second mode of operation, including comparing an output of the inductive switching supply to a specified output reference to provide an error signal indicative of the comparison and in response, adjusting one or more of the charge phase duration, or the dump phase during using information about the error signal.

In Example 18, the subject matter of one or any combination of Examples 12-17 can optionally include controlling the state of the switch, in the second mode of operation, includes comparing an output of the inductive switching supply to a specified output reference to provide an error signal indicative of the comparison, and in response, adjusting a repetition rate of successive charge and dump phases using information about the error signal.

In Example 19, the subject matter of one or any combination of Examples 12-18 can optionally include adjusting the implantable medical device back to the first mode of operation when information about the detected magnetic field indicates the implantable medical device is no longer exposed to an intense magnetic field.

In Example 20, the subject matter of one or any combination of Examples 12-19 can optionally include at least one of the comparing an inductor current to a specified peak current threshold or comparing the inductor current to a specified minimum inductor current threshold including using a first bias circuit when the implantable medical device is in the first mode of operation, and using a second bias circuit when the implantable medical device is in a second mode of operation, the second bias circuit is configured to reduce a latency of the comparing, in the second mode of operation, as compared to the first mode of operation.

These examples can be combined in any permutation or combination. This overview is intended to provide an overview of subject matter of the present patent application. It is not intended to provide an exclusive or exhaustive explanation of the invention. The detailed description is included to provide further information about the present patent application.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Nuclear magnetic resonance (NMR) devices (e.g., an MRI scanner, an NMR spectrometer, or other NMR device) can produce both static and time-varying magnetic fields. For example, an MRI scanner can provide a strong static magnetic field, $B_0$, such as to align nuclei within a subject to the axis of the $B_0$ field. The $B_0$ can provide a slight net magnetization (e.g., a "spin polarization") among the nuclei in bulk because the spin states of the nuclei are not randomly distributed among the possible spin states. Because the resolution attainable by NMR devices can be related to the magnitude of the $B_0$ field, a stronger $B_0$ field can be used to spin polarize the subject's nuclei to obtain finer resolution images. NMR devices can be classified according the magnitude of the $B_0$ field used during imaging, such as a 1.5 Tesla $B_0$ field, a 3.0 Tesla $B_0$ field, etc.

After nuclei are aligned using the $B_0$ field, one or more radio frequency (RF) magnetic excitation pulses can be delivered such as to alter the alignment of specified nuclei (e.g., within a particular volume or plane to be imaged within the subject). The power, phase, and range of frequencies of the one or more RF excitation pulses can be selected, such as depending on the magnitude of the $B_0$ field, the type or resonant frequency of the nuclei to be imaged, or one or more other factors. After the RF excitation pulses are turned off, one or more RF receivers can be used to detect a time-varying magnetic field (e.g., a flux) developed by the nuclei as they relax back to a lower energy state, such as the spin polarized state induced by the static magnetic field, $B_0$.

One or more gradient magnetic fields can also be provided during MR, such as to create a slight position-dependent variation in the static polarization field. The variation in the static polarization field slightly alters the resonant frequency of the relaxing nuclei, such as during relaxation after excitation by the one or more RF pulses. Using the gradient field along with the static field can provide "spatial localization" of signals detected by the RF receiver, such as by using frequency discrimination. Using a gradient field allows a volume or plane to be imaged more efficiently. In a gradient field example, signals received from relaxing nuclei can include energy in respective unique frequency ranges corresponding to the respective locations of the nuclei.

Active MRI equipment can induce unwanted torques, forces, or heating in an IMD or other conductive implant, or can interfere with operation of the IMD. In certain examples, the interference can include disruption in sensing by the IMD, interference in communication between the IMD and other implants or external modules during MRI operation, or disruption in monitoring or therapeutic function of the IMD.

During an MRI scan, the one or more RF excitation pulses can include energy delivered at frequencies from less than 10 MHz to more than 100 MHz, such as corresponding to the nuclear magnetic resonances of the subject nuclei to be imaged. The gradient magnetic field can include energy delivered at frequencies lower than the RF excitation pulses, because most of the AC energy included in the gradient field is provided when the gradient field is ramping or "slewing." The one or more gradient magnetic fields can be provided in multiple axes, such as including individual time-varying gradient fields provided in each of the axes to provide imaging in multiple dimensions.

In an example, the static field, $B_0$, can induce unwanted forces or torques on ferromagnetic materials, such as steel or nickel. The forces or torques can occur even when the materials are not directly within the "bore" of the MRI equipment—because significant fields can exist near the MRI equipment. Moreover, if an electric current is switched on or off in the presence of the $B_0$ field, a significant torque or force can be suddenly imposed in the plane of the circulation of the current, even though the $B_0$ field itself is static. The induced force or torque can be minimal for small currents, but the torque can be significant for larger currents, such as those delivered during defibrillation shock therapy. For example, assuming the circulating current is circulating in a plane normal (e.g., perpendicular) to the static field, the torque can be proportional to the magnitude of the $B_0$ field, multiplied by the surface area of the current loop, multiplied by the current.

Time-varying fields, such as the gradient field or the field associated with the RF excitation pulse, can present different risks than the static field, $B_0$. For example, the behavior of a wire loop in the presence of a time-varying magnetic field can be described using Faraday's law, which can be represented by $$\varepsilon = -\frac{d\Phi_{B_1}}{dt},$$

in which ε can represent the electromotive force (e.g., in volts), such as developed by a time-varying magnetic flux. The magnetic flux can be represented as $$\Phi_{B1} = \iint_S B_1 \cdot dS,$$

in which $B_1$ can represent an instantaneous magnetic flux density vector (e.g., in Webers per square meter, or Tesla). If $B_1$ is relatively uniform over the surface S, then the magnetic flux can be approximately $\Phi_{B1}=|B_1||A|$, where A can represent the area of the surface S. Operating MRI equipment can produce a time-varying gradient field having a slew rates in excess of 100 Tesla per second (T/s). The slew rate can be similar to a "slope" of the gradient field, and is thus similar to $$\frac{d\Phi_{B1}}{dt}.$$

The electromotive force (EMF) of Faraday's law can cause an unwanted heating effect in a conductor—regardless of whether the conductor is ferromagnetic. EMF can induce current flow in a conductor (e.g., a housing of the IMD, one or more other conductive regions within the IMD, or one or more other conductive implants). The induced current can dissipate energy and can oppose the direction of the change of the externally applied field (e.g., given by Lenz's law). The induced current tends to curl away from its initial direction, forming an "eddy current" over the surface of the conductor, such as due to Lorentz forces acting upon electrons moving through the conductor. Because non-ideal conductors have a finite resistivity, the flow of induced current through the conductor can dissipate heat. The induced heat can cause a significant temperature rise in or near the conductor over the duration of the scan. The power dissipated by the eddy current can be proportional to the square of both the peak flux density and the frequency of the excitation.

Generally, induced currents, such as induced by the RF magnetic excitation pulse, can concentrate near the surface of a conductor, a phenomenon that can be referred to as the skin effect. The skin effect can limit both the magnitude and depth of the induced current, thus reducing power dissipation. However, the gradient field can include energy at a much lower frequency than the RF magnetic excitation field, which can more easily penetrate through the housing of the IMD. Unlike the field from the RF excitation pulse, the gradient field can more easily induce bulk eddy currents in one or more conductors within the IMD housing, such as within one or more circuits, capacitors, batteries, or other conductors.

Aside from heating, the EMF can create, among other things, non-physiologic voltages that can cause erroneous sensing of cardiac electrical activity, or the EMF can create a voltage sufficient to depolarize cardiac tissue or render the cardiac tissue refractory, possibly affecting pacing therapy. In an illustrative example, the IMD can be connected to one or more leads, such as one or more subcutaneous or intravascular leads positioned to monitor the patient, or to provide one or more therapies to the patient. In this illustrative example, a surface area of a "circuit" including the lead, the housing of the IMD, and a path through at least partially conductive body tissue between an electrode on the lead and the IMD housing can be more than 300 square centimeters, or more than 0.03 square meters. Thus, using Faraday's law, the electromotive force (EMF) developed through the body tissue between the electrode (e.g., a distal tip or ring electrode) of the lead and the housing of the IMD can be more than 0.03 square meters times 100 t/s, or more than 3 volts.

In an example, the IMD can include one or more power supplies, such as one or more relatively high-efficiency switching power supplies. The present inventors have also recognized, among other things, that the operation of an inductive switching supply can be altered by the presence of externally-applied electromagnetic fields, such as one or more of the static, the spatial gradient, or the RF magnetic excitation field, such as used by the NMR equipment.

In an example, the IMD can include an inductive switching power supply having more than one mode, such as a first mode (e.g., a non-MRI mode) and a second mode (e.g., an MRI-mode). In the non-MRI mode, the switching supply can use an inductor with an unsaturated ferromagnetic core. In the MRI mode, the switching supply can use an inductor with a saturated core or with a reduced inductor value, such as by adjusting one or more operating parameters including one or more of a comparator bias, a peak or minimum inductor current, or a duration of one or more of a charge phase or dump phase of operation, or another parameter.

In an example, an inductor, such as included in the power supply of the IMD, can be constructed with a ferromagnetic core in order to increase inductance. The inductance of the inductor can be effectively multiplied by the core permeability. However, under an intense magnetic field, such as the static field used by NMR equipment, the ferromagnetic core can saturate, which can dramatically lower the inductance. Such an intense magnetic field can be on the order of 1 Tesla or more, or another magnetic field intensity, such as intense enough to saturate the inductor or otherwise interfere with operation of the power supply, or one or more other IMD circuits. In an example, the IMD can include a magnetic detector, such as a core saturation detector, such as to detect a loss of inductance in the power inductor. In an example, one or more operating parameters of the inductive supply can be adjusted, such as in response to a detected magnetic field.

Figure 1:
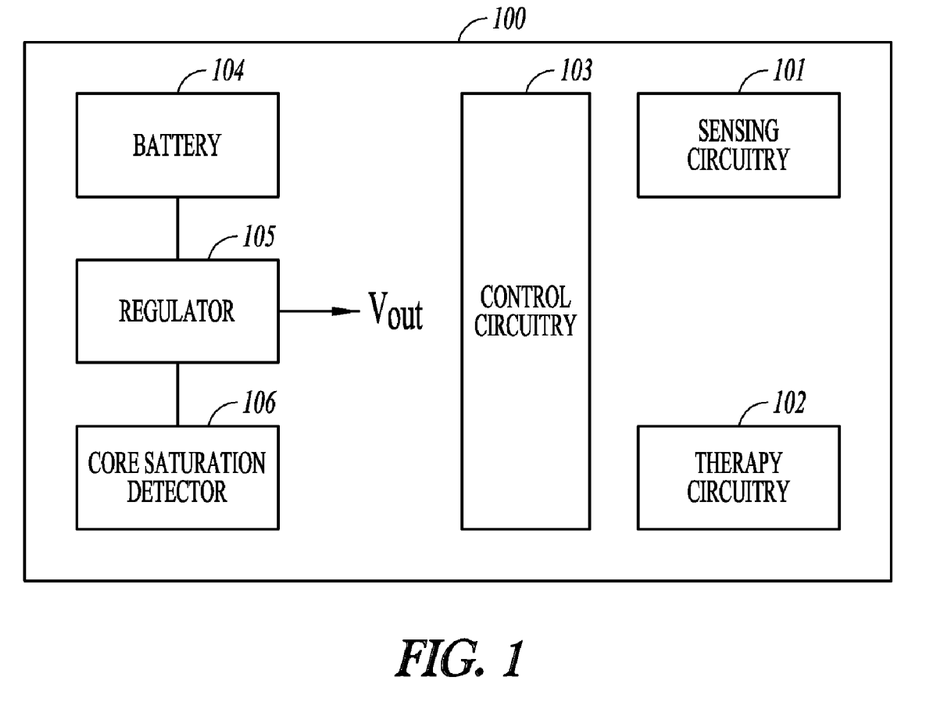
FIG. 1 illustrates generally an example of portions of a system that can include an ambulatory or implantable medical device (IMD), such as cardiac function management device.

FIG. 1 illustrates generally an example of portions of a system that can include an ambulatory or implantable medical device (IMD) 100, such as cardiac function management device. In FIG. 1, a sensing circuit 101 can receive signals indicative of cardiac electrical activity (e.g., cardiac electrogram information), such as from subcutaneous or intravascular electrodes, such as implanted in the heart. In an example, a therapy circuit 102 can include a pulse generation circuit, such as for generating one or more pacing pulses or defibrillation shocks, or other electrostimulation therapy signals, such as to be delivered to the heart via the electrodes. A control circuit 103 can interpret the electrogram signals, such as to control the output of electrical stimulation to heart as needed in accordance with a normal operating mode. The power supply for the device 100 can include a battery 104 and one or more inductive switching supplies, such as an inductive switching supply 105. The inductive switching supply 105 can be a DC-DC converter, such as configured to provide a specified regulated output voltage range $V_{out}$ to the electronic circuitry of the device 100, such as to power one or more of the sensing, therapy, or control circuitries, or one or more other circuits or portions of the device 100.

In an example, a core saturation detector 106 can monitor one or more parameters of operation of the switching supply, such as one or more parameters that can vary as the inductance of the power inductor changes. For example, when a strong magnetic field is present, such as produced by an NMR device, the core of the power inductor can saturate, such as causing the inductance of the inductor to decrease. The resulting decrease in inductance can then be detected by the core saturation detector 106, such as to allow the device 100 to modify its operation. In an example, upon detection of core saturation, the device can be configured to enter an MRI mode that can include, among other things, switching to a non-sensing fixed-rate bradycardia pacing mode (e.g., VOO), disabling of a tachyarrhythmia therapy, or adjusting or varying one or more other operating parameters such as to place the IMD in a conditionally safe mode to preserve operation in an environment including intense electromagnetic fields. In an example, the device 100 can be configured to automatically exit the MRI mode, such as when one or more electromagnetic sensors, such as a magnetic detector, (e.g., a Hall effect sensor, or the core saturation detector), indicate that the intense magnetic field is no longer present.

In an example, the core saturation detector 106 can measure the time duration of one or more phases of the supply's power conversion cycle, such duration which can depend upon the inductance of the power inductor, such as when the supply is operating in a current-limiting mode. In an example, the core saturation detector 106 can measure the peak power inductor current in inductive supplies operating in other modes. In an example, the control circuitry and core saturation detector may be implemented by discrete component circuitry or a microprocessor-based controller, such as executing coded instructions stored in a memory circuit or other processor-readable medium.

Figure 2:
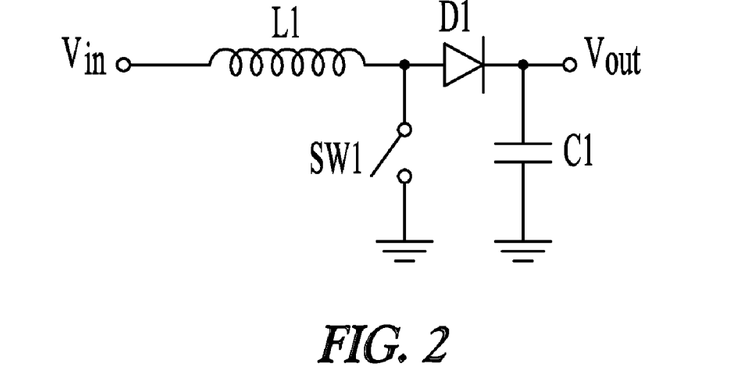
FIG. 2 illustrates generally an example of a boost configuration inductive switching supply, such as included in an ambulatory or implantable medical device (IMD).

FIG. 2 illustrates generally an example of an inductive switching supply having a boost configuration, such as included in an ambulatory or implantable medical device (IMD). An inductive switching supply can include one or more inductors, such as including a ferromagnetic core. The ferromagnetic core can increase an inductance as compared to an inductor with about the same number of wire turns wound around an air core (or another non-ferromagnetic material). In an example, the introduction of the ferromagnetic core material can increase the inductance, such as by a factor such as representing the relative magnetic permeability of the inductor core material. In an example, in the presence of an intense externally-applied magnetic field, many of the magnetic domains in the ferromagnetic core material can align with this magnetic field, causing the core to become "saturated," or causing a reduction in the inductance. In an example, when the inductor core is saturated, the effective inductance value of the inductor can drop dramatically (e.g., the relative magnetic permeability of the core material, can drop to around 1.0). For example, the saturation or decrease in inductance of the inductor can alter the efficiency or operating characteristics of the inductive switching supply.

In an example, the inductive switching supply can alternately store and discharge energy, such as using an inductor, in a two-phase power conversion cycle. For example, the power conversion phases can be designated as fill (e.g., charge) and dump (e.g., discharge) phases, respectively. Inductive switching supplies can be configured in a variety of topologies. For example, three different inductive switching supply topologies can include: buck (e.g., step-down), boost (e.g., step-up), or buck-boost (e.g., inverting, having an input voltage magnitude lower or higher than the output voltage magnitude). In an example, the inductive energy storage element need not be a single-winding inductor. For example, the inductive switching supply can include a transformer as the inductive element, and the term inductor can be used to describe many different energy storage circuits, such as used to store energy magnetically, such as including a reactor, an inductor, a transformer, or the like.

In the example of FIG. 2, an inductive switching supply having a boost configuration is shown. In an example, during the fill phase, the switch SW1 can close, and the input voltage $V_{in}$ can be impressed across an inductor L1. In FIG. 2, a diode D1 can prevent a capacitor C1 from discharging to ground. In an example, such as when the input voltage is supplied from a battery or other supply providing a relatively constant voltage, the current through the inductor L1 can increase with time, such as at a rate that proportional to the input voltage divided by the inductance of the inductor L1. In an example, the energy stored in the inductor during the fill phase can be about equal to one-half the inductance times the square of the peak current.

In an example, switch SW1 can be opened after the charge phase, such as during the dump phase. In an example, during the dump phase, the voltage across the inductor L1 adjusts to maintain continued current flow, such as because the inductor current cannot change instantaneously. Thus, in order for current to continue flowing, the inductor voltage can change enough to forward-bias the diode D1. In an example, the switch SW1 can be repeatedly opened and closed, such as to produce a sequence of power conversion cycles, and the voltage $V_{out}$ across the capacitor C1 can rise with every cycle as the capacitor is charged by the inductor current.

Figure 3:
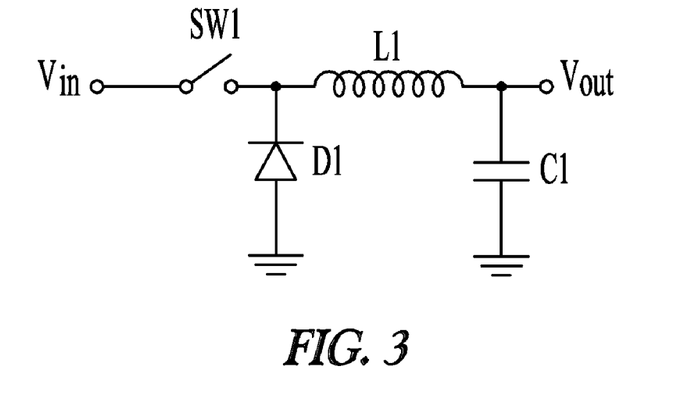
FIG. 3 illustrates generally an example of a buck configuration inductive switching supply, such as included in an ambulatory or implantable medical device (IMD).

FIG. 3 illustrates generally an example of a buck configuration inductive switching supply, such as included in an ambulatory or implantable medical device (IMD). In an example, circuitry, such as described in FIG. 2, can be rearranged to the buck configuration, such as shown in FIG. 3. In this configuration, the switch SW1 can close during the fill phase, and a voltage represented by ($V_{in}$–$V_{out}$) can be impressed across the inductor L1, such as causing the inductor current to increase. In an example, the inductor current can charge an output capacitor C1, during the fill phase. In an example, the switch SW1 can open to start the dump phase, such as causing the voltage across the inductor L1 to adjust itself to maintain current flow, which then charges the output capacitor C1 through the diode D1.

Figure 4:
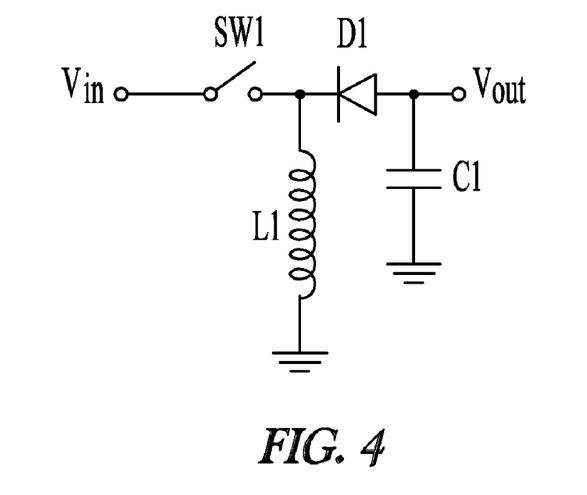
FIG. 4 illustrates generally an example of a buck-boost configuration inductive switching supply, such as included in an ambulatory or implantable medical device (IMD).

FIG. 4 illustrates generally an example of a buck-boost configuration inductive switching supply, such as included in an ambulatory or implantable medical device (IMD). In an example, locations of the inductor and diode in the circuit of FIG. 3 can be swapped, such as to provide the inverting or buck-boost configuration of the example of FIG. 4. In this configuration, when the switch SW1 closes to start the fill phase, $V_{in}$ is impressed across the inductor, making the inductor current ramp up. When the switch opens to start the dump phase, the current flow is maintained by the voltage across the inductor. The inductor current during the dump phase can then flow through the diode and can charge the output capacitor to an output voltage $V_{out}$, such as having the opposite polarity as the input voltage $V_{in}$.

Figure 5:
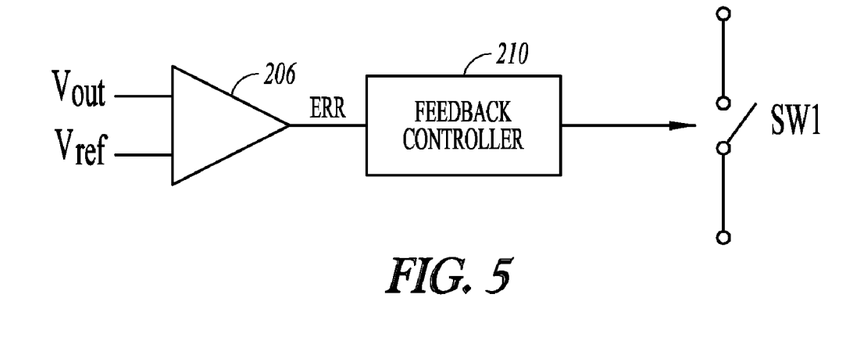
FIG. 5 illustrates generally an example of a feedback control system for an inductive switching supply, such as included in an ambulatory or implantable medical device (IMD).

FIG. 5 illustrates generally an example of a feedback control system for an inductive switching supply, such as included in an ambulatory or implantable medical device (IMD). A feedback control system may be used to regulate the output voltage $V_{out}$ in any of the examples of FIGS. 2-4, such as by controlling the switch SW1 using information about an error signal. FIG. 5 includes a comparator 206 that can compare the instantaneous output voltage $V_{out}$ with a reference voltage $V_{ref}$ such as to generate an error signal ERR. In an example, the error signal ERR can be provided to a feedback controller 210. For example, the controller 210 can control the state of the switch SW1, such as to reduce the error signal.

The feedback controller can be configured to operate using various control laws or modes. For example, in a clocked frequency modulation control mode, the feedback controller can gate an oscillator to operate the switch SW1 and generate power conversion cycles, such as to reduce the error signal ERR, such as controlling a pulse repetition rate or frequency of switching control pulses (e.g., increasing or decreasing a number of successive fixed pulse-width signals over a specified duration such as to cycle SW1 more or less often during the specified duration).

In an example, in a current-limited frequency modulation control mode, the feedback controller 210 can control the switch SW1 to generate power conversion cycles, such as to reduce the error signal ERR, such as by controlling durations of the fill and dump phases using information about the inductor current. For example, the switch SW1 can be operated so that the inductor current increases during the fill phase until a specified peak current value is reached and then decreases during the dump phase to zero or some other predetermined value. In an example, in an on-demand current-limited control mode, the feedback controller can inhibit power conversion cycles when the output voltage is at or above a specified output voltage, and the feedback controller can trigger or begin one or more conversion cycles, such as when the output voltage falls below the specified output voltage.

In an example, in a pulse-width modulation control mode, the feedback controller operates the switch SW1 at a fixed frequency but varies the durations of the fill and dump phases to decrease the error signal (i.e., increases the duration of the fill phase to increase the output voltage and vice-versa).

Figure 6:
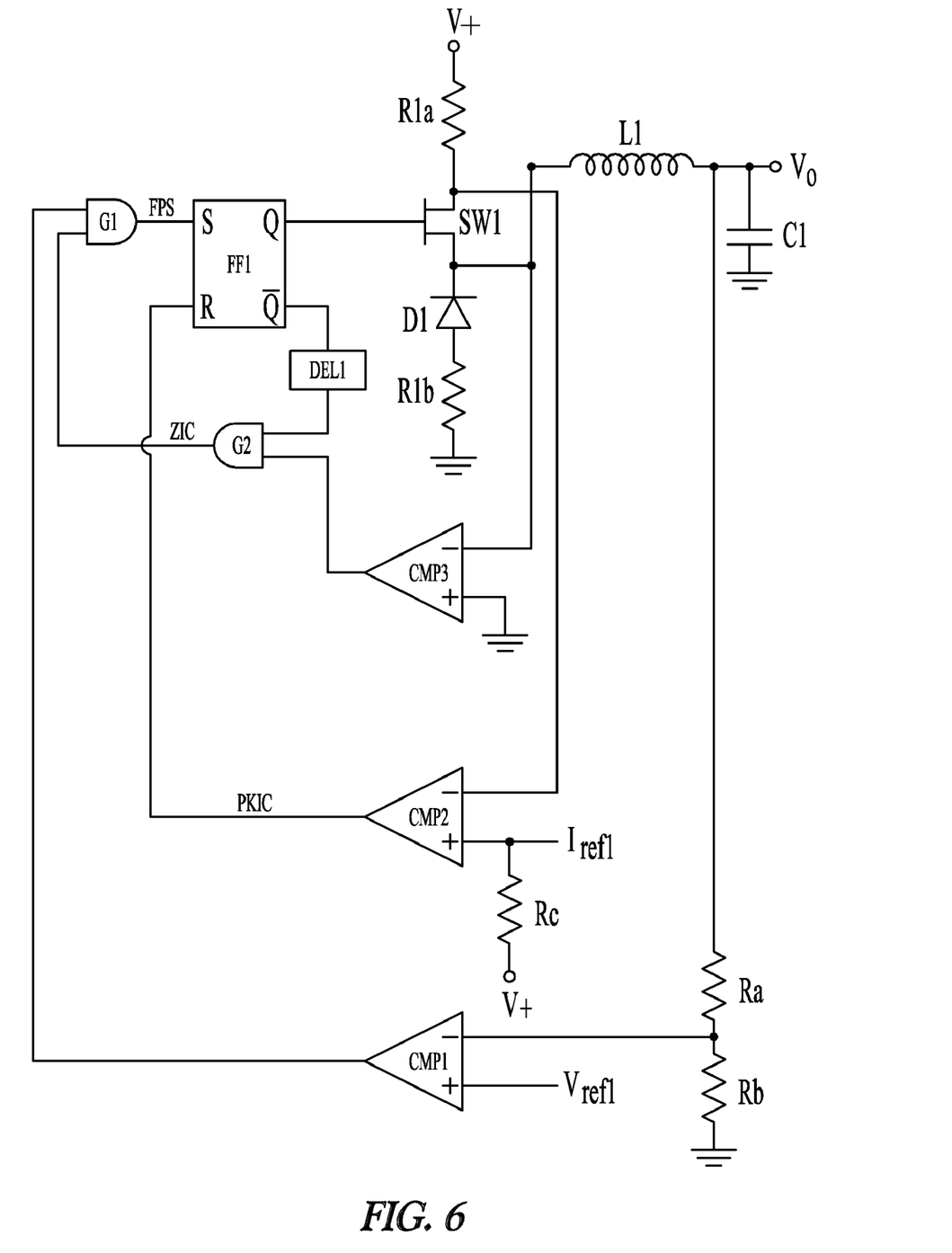
FIG. 6 illustrates generally an example of a buck configuration inductive switching supply operating in a current-limited control mode, such as included in an ambulatory or implantable medical device (IMD).
Figure 7:
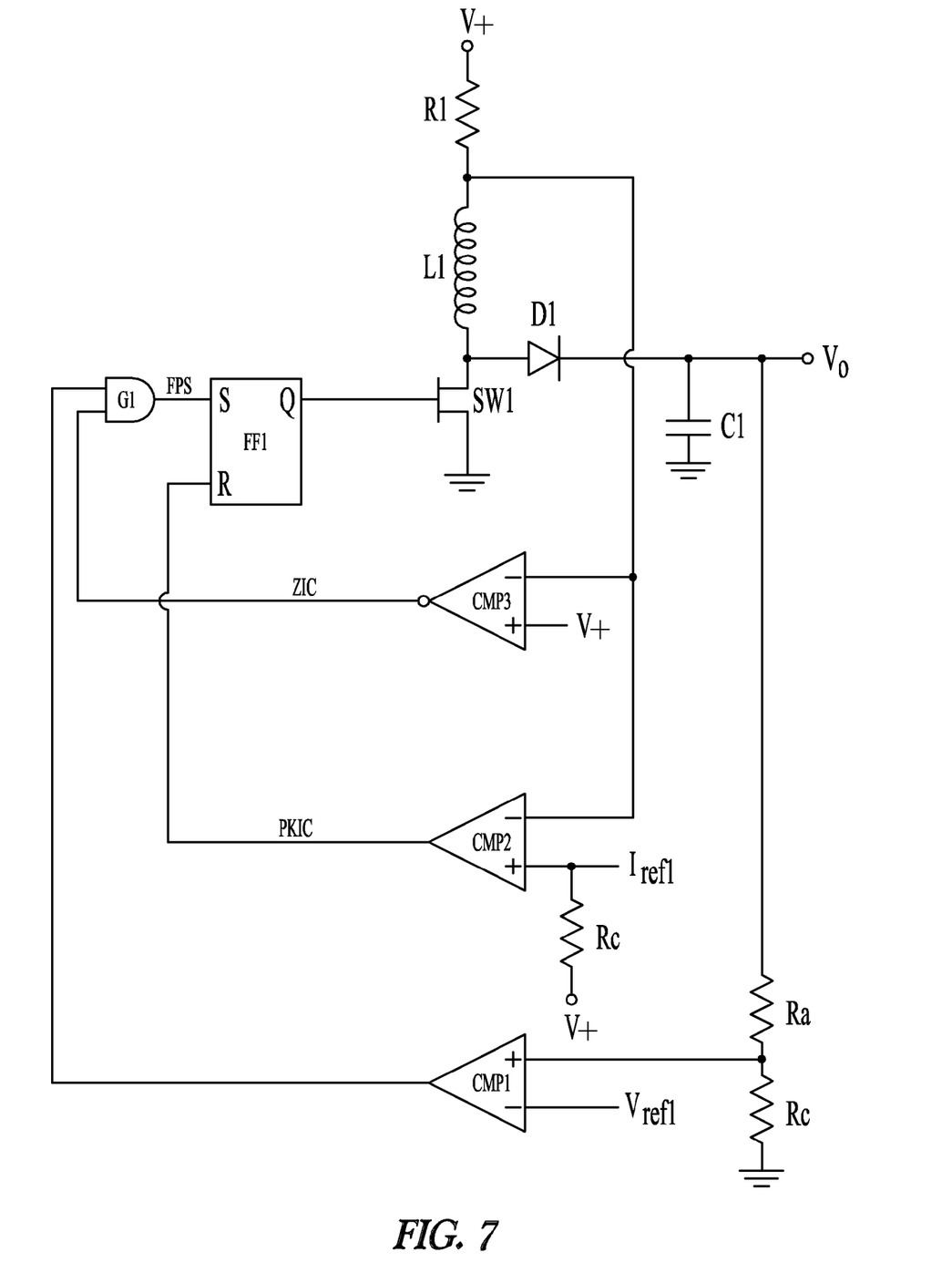
FIG. 7 illustrates generally an example of a boost configuration inductive switching supply operating in a current-limited control mode, such as included in an ambulatory or implantable medical device (IMD).
Figure 8:
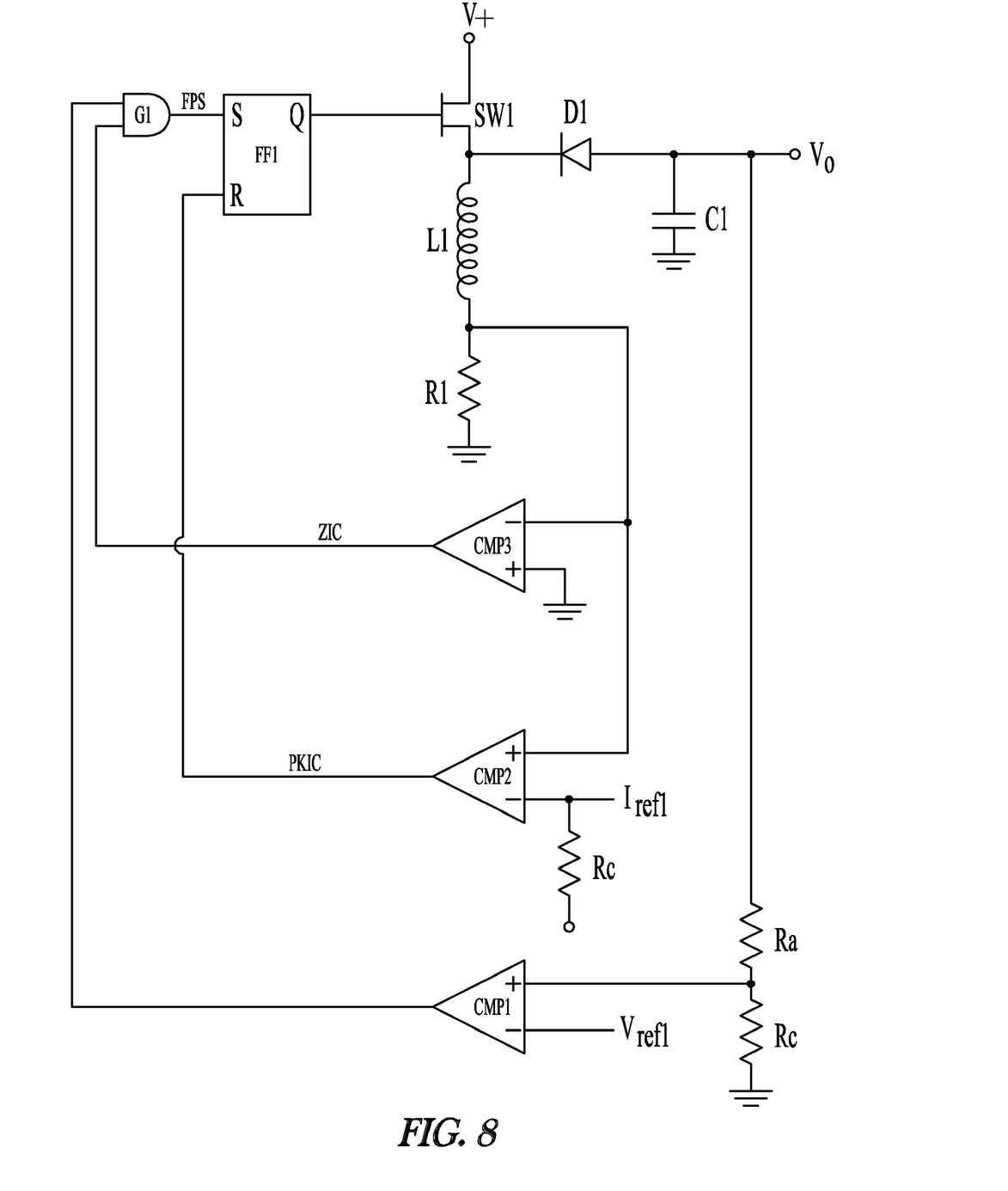
FIG. 8 illustrates generally an example of a buck-boost configuration inductive switching supply operating in a current-limited control mode, such as included in an ambulatory or implantable medical device (IMD).

FIG. 6-8 illustrate generally respective examples of a buck configuration inductive switching supply, a boost configuration inductive switching supply, and a buck-boost configuration inductive switching supply, each respectively operable in a current-limited control mode, or one or more other modes or according to one or more other specified control laws, such as included in an ambulatory or implantable medical device (IMD).

As discussed above, exposure to an intense magnetic field can saturate an inductor's ferromagnetic core, or can dramatically reduce the inductance of the inductor. Thus, reduced inductance can allow a much higher rate of change in inductor current during each power conversion phase. In a switching supply, such as operating in a current-limited pulse frequency modulated control mode this can cause the fill and dump phases to occur more frequently, with each having a shorter respective duration, and the energy delivered to the load per power conversion cycle can be much lower as the energy storage of an inductor can be represented by: $0.5*L*I^2$. Similarly, for a switching supply operating in a clocked pulse frequency modulation control mode or a pulse width modulation control mode, the peak inductor current during a power conversion cycle can increase dramatically as the inductance decreases, such as due to exposure to the intense magnetic field.

An inductive switching supply operating in a current-limited control mode, such as shown in the various configurations of FIGS. 6-8, can be configured to generate, among others, three signals such as indicating the start and end of the power conversion phases, such as for use by the core saturation detector of FIG. 1. For example, FPS (e.g., "Fill Phase Start") can indicate the start of the fill phase, PKIC (e.g., "Peak Inductor Current") can indicate that the inductor current has reached a specified peak value and can be used to control the end of the fill phase or the start of the dump phase, and ZIC (e.g., "Zero Inductor Current") can indicate that the inductor current is at or near zero and can be used to control the end of the dump phase. In an example, the core saturation detector 106 can measure the length of the fill or dump phase, such as using information about the time intervals between FPS and PKIC or between PKIC and ZIC, respectively.

In the examples of FIGS. 6-8, the inductive switching supply circuits can operate using a current-limited frequency control mode in buck, boost, and buck-boost configurations, respectively. The examples of FIGS. 6-8 can each include one or more of a respective inductor L1, a respective switch SW1, a respective capacitor C1, and a respective diode D1. In an example, when one or more of FIGS. 6-8 uses a current-limited control mode (e.g., either synchronously, such as trigged by or using one or more clocks or timers, or asynchronously), the duration of the fill and dump phases during a power-conversion cycle can be controlled, such as via feedback from an inductor L1 current monitor. For example, during the fill phase, the inductor current can be near zero and can ramps upwards, such as towards a specified peak current value. In an example, once the specified peak current value is reached (such as detected by one or more comparators), the fill phase can be terminated and, for example, a dump phase can begin. In an example, during the dump phase, the inductor L1 current can be around the specified peak current value, and can ramp back down towards zero. In an example, when the inductor current reaches zero (such as detected by one or more comparators), the dump phase can be terminated. In an example, further successive fill-dump cycles can be initiated or suppressed, such as by using feedback. In an example, the feedback can include sensing one or more of an output current or voltage, and comparing the output current or voltage with a reference, such as to provide an error signal.

In the example of FIG. 6, (e.g., the buck configuration), a MOS switch SW1 can be controlled by the output of a flip-flop FF1, such as to switch a battery (or other input) voltage $V_+$ across inductor L1 and capacitor C1. In an example, the capacitor C1 voltage can be the output voltage $V_o$ of the supply. For example, when the switch SW1 closes, the fill phase can begin, and the inductor current can increase, such as providing a roughly constant voltage across the inductor L1. In an example, when the switch SW1 opens, the fill phase can end and the dump phase can begin. For example, during the dump phase, the voltage across the inductor L1 can reverse polarity, such as to maintain the flow of inductor current (because the inductor current cannot change instantaneously). Thus, the current through the inductor L1 can flow through diode D1, and can decrease, such as assuming a roughly constant voltage across the inductor.

In an example, the durations of the fill and dump phases can be controlled by circuitry, such as using information about the inductor current. For example, a portion of the output voltage $V_o$ can be fed back, such as via a voltage divider made up of resistors $R_a$ and $R_b$, such as to a comparator CMP1. In an example, the fed back voltage can be compared, such as to a reference voltage $V_{ref1}$. In an example, if the output voltage is low, the output of CMP1 can be asserted, and a power conversion cycle can be triggered. The inductor L1 current can be measured, such as using current sense resistors R1a or R1b. In an example, the voltage across current sense resistors R1a or R1b can be fed to respective comparators CMP2 or CMP3.

In an example, such as during the dump phase, the inverted output of comparator CMP3 can be asserted when the inductor current is zero, such as indicated by the assertion of an AND gate G2, such as to provide the signal ZIC. In an example, comparator CMP3 can have a small negative input offset voltage, such as to ensure that the ZIC signal is asserted when the inductor current is zero. In an example, a delay element DEL1 and the AND gate G2 can gate the output of comparator CMP3, such as to ensure that the signal ZIC is only used when the output of comparator CMP3 is valid. In an example, the AND gate G2, the comparator CMP3, and the delay element DEL1 can be used as a zero current detector circuit. For example, the rising edge of signal ZIC can indicate that the previous dump cycle has ended, such as because the inductor current has decreased to about zero.

In an example, the outputs of the gate G2 and the comparator CMP1 can be ANDed together, such as using an AND gate G1, such as to provide the FPS signal, such as to trigger the fill phase, such as by setting a flip-flop FF1. In an example, the flip-flop FF1 can include an output that can be used to control the state of switch SW1. In an example, the fill phase can continue, such as until the inductor current, which flows through sense resistor R1a during the fill phase, reaches a specified peak value. The voltage across resistor R1a can be compared to a voltage, such as derived from a reference current $I_{ref1}$, such as using a comparator CMP2. For example, the reference current $I_{ref1}$ can run through a resistor Rc. In an example, the values of the reference current $I_{ref1}$ or the resistor Rc can be specified, such as to provide the output PKIC from comparator CMP2 when the inductor current reaches or exceeds the specified peak value. In an example, the comparator CMP2, and the resistors R1a and Rc can be used as a peak current detector circuit. In an example, the assertion of PKIC can be used to reset the flip-flop FF1, such as to indicate the end of the fill phase and the beginning of the dump phase.

In the examples of FIGS. 7-8, components similar to FIG. 6 can be included, such as to provide respective inductive switching supplies in boost and buck-boost configurations, respectively, the operations of which can be similar to that of the buck configuration of FIG. 6. For example, a start of the fill phase, an end of the fill phase, or an end of the dump phase can be respectively controlled or indicated, such as by assertions of the FPS, PKIC, or ZIC signals, respectively, or using one or more other signals. In the examples of FIGS. 7-8, a current sense resistor R1 and an AND gate G1 can be used to implement the inductor current monitor circuit.

In an example, the length of the fill phase can be measured, and can be compared to a threshold value, such as to determine if core saturation exists, or to determine if the inductor L1 inductance is decreasing dramatically. For example, in a boost or inverting configuration (e.g., FIGS. 7-8), the battery or input voltage can be impressed across the inductor L1 during the fill phase. If the battery voltage does not change significantly during the fill phase of an individual charging cycle, then the inductor current can exhibit a fairly constant rate of change (dI/dt) during the fill phase. That is, the inductor current can change roughly linearly if the voltage across the inductor is roughly constant. The duration of the fill phase $t_{fill}$ can be linearly related to the inductance L of the inductor L1, such as represented approximately by:

$$t_{fill} = (I_{peak} * L)/V_+$$

where $I_{peak}$ can represent the specified peak value of the inductor current and $V_+$ can represent a roughly constant battery voltage. For example, when the inductor core saturates, L can be reduced by a factor of about $\mu_m$, (e.g., the relative magnetic permeability of the core material). In an illustrative example, the following parameters can be used:
L=300 µH
$I_{peak}$=50 mA
$V_+$=3 V
$\mu_m$=50

In this illustrative example, during normal operation, the fill phase duration can be represented by:

$$t_{fill} = (I_{peak}*L)/V_+ = (50\text{ mA})(300\text{ µH})/(3\text{ V}) = 5\text{ µs}$$

But, in this illustrative example, when the inductor core saturates or when the inductance drops dramatically (e.g., from 300 µH to 6 µH), the fill phase duration can be reduced, and can be represented by:

$$t_{fill} = (I_{peak}*L)/V_+ = (50\text{ mA})(6\text{ µH})/(3\text{ V}) = 100\text{ ns}$$

Thus, in an example, a saturation detection threshold can be $t_{fill}<1$ µs, and, for example, a core saturation detector can declare a core saturation when $t_{fill}<1$ µs.

In an example, the length of the dump phase can be measured and compared, such as to a threshold value, such as to determine if core saturation exists or to determine if the inductor L1 inductance is decreasing dramatically. For example, in a buck configuration (e.g., FIG. 6), the output voltage can be impressed across the inductor L1, such as during the dump phase (such as neglecting the forward bias voltage of the diode D1). The duration of the dump phase $t_{dump}$ can then be linearly related to the inductance L of the inductor L1, such as represented approximately by:

$$t_{dump} = (I_{peak}*L)/V_{out}$$

where $I_{peak}$ can represent the specified peak value of the inductor current and $V_{output}$ can represent a roughly constant battery voltage. In an illustrative example, when the inductor core saturates, L can be reduced, such as by a factor of $\mu_m$ (the relatively magnetic permeability of the core material). In this illustrative example, the following parameters can be used:

$L = 300 \, \mu H$
$I_{peak} = 25 \, mA$
$V_{output} = 3 \, V$
$\mu_m = 50$

In this illustrative example, during normal operation, the dump phase duration can be represented by:

$$t_{dump} = (I_{peak} * L)/V_{output} = (25 \, mA)(300 \, \mu H)/(3 \, V) = 2.5 \, \mu s$$

But, in this illustrative example, when the inductor core saturates or when the inductance drops dramatically (e.g., from 300 µH to 6 µH), the dump phase duration can be reduced, and can be represented by:

$$t_{dump} = (I_{peak} * L)/V_{output} = (25 \, mA)(6 \, \mu H)/(3 \, V) = 50 \, ns$$

Thus, in an example, a saturation detection threshold can be $t_{dump} < 0.5 \, \mu s$, and, for example, a core saturation detector can declare a core saturation when $t_{dump} < 0.5 \, \mu s$.

In an example, in a current-limited switching supply in either a buck, boost, or inverting configuration (e.g., FIGS. 6-8), the core saturation detector 106 can be used to measure the length of the fill phase $t_{fill}$, such as using information about the time interval between the assertions of the FPS signal and the PKIC signal, or one or more other signals. Similarly, in an example, the dump phase $t_{dump}$ can be determined, such as using information about the time interval between the assertions of PKIC and ZIC, or the total power conversion cycle time as the time interval between the assertions of FPS and ZIC, or using one or more other signals.

In an example, the core saturation detector can compare one or more measured time intervals to one or more specified threshold values, such as to determine if core saturation exists. In an example, one or more portions or parts of the comparison can be implemented programmatically, or such as using one or more circuits. In an example, the core saturation detector can include one or more timers, counters, or delay elements, such as to establish one or more minimum allowable time intervals between starting and stopping events (e.g., a minimum fill phase duration, a minimum dump phase duration, or one or more intervals). In an example, the core saturation detector can include a counter, such as is started or reset by one phase signal and stopped by another phase signal (e.g., started and reset by FPS and stopped by PKIC, such as to measure the fill phase duration). For example, the counter's value can be compared to a specified threshold value. In an example, if the counter's value is at or above the threshold, a bit can be set, such as readable by the controller, such as to indicate core saturation.

In an example, in any of the topologies of FIGS. 6-8, the diode D1 (e.g., a "catch diode" or "commutating diode") can be replaced with a switch or other device (e.g., one or more transistors), such as to provide a controllable or switchable connection, such as controllable by voltage or current feedback as discussed in FIGS. 5-8. For example, in FIG. 6, D1 can be replaced with a switch controlled by a logical inverse of the zero inductor current (ZIC) signal. Similarly, in the examples of FIGS. 7-8, D1 can be replaced with a switch controlled by a signal such as provided by a logical NOR of the FF1 Q output and the ZIC signal.

Figure 9:
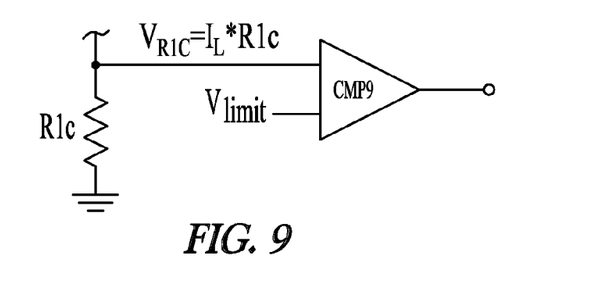
FIG. 9 illustrates generally an example of components for measuring inductor current in order to detect core saturation, such as included in an ambulatory or implantable medical device (IMD).

FIG. 9 illustrates generally an example of components for measuring inductor current in order to detect core saturation, such as included in an ambulatory or implantable medical device (IMD). In examples of an inductive switching supply, such as operating in a clocked frequency modulation or a pulse-width modulation control mode, the peak inductor current during a power conversion cycle can increase drastically if the inductor core saturates. In order to detect core saturation, the current through the inductor in any of the buck, boost, or inverting configurations can be measured and compared with a specified threshold value.

For example, the specified threshold can be set to value well above any inductor current value expected to occur under normal operating conditions. In an example, the inductor current can be measured such as using similar components or techniques to those used to measure inductor current for the current-limited control modes such as included in the examples of FIGS. 6-8. For example, FIG. 9 includes an example in which the voltage across a current sense resistor R1c can be fed to a comparator CMP9, such as when the voltage is approximately equal to $R1c * I_L$, where $I_L$ can represent the inductor current. For example, if the voltage across the resistor R1c exceeds a specified limit value $V_{limit}$, such as corresponding to an inductor current above the specified threshold value, core saturation can be declared as detected. In an example, the output of the comparator CMP9 can be used to set a bit readable by the controller.

Figure 10:
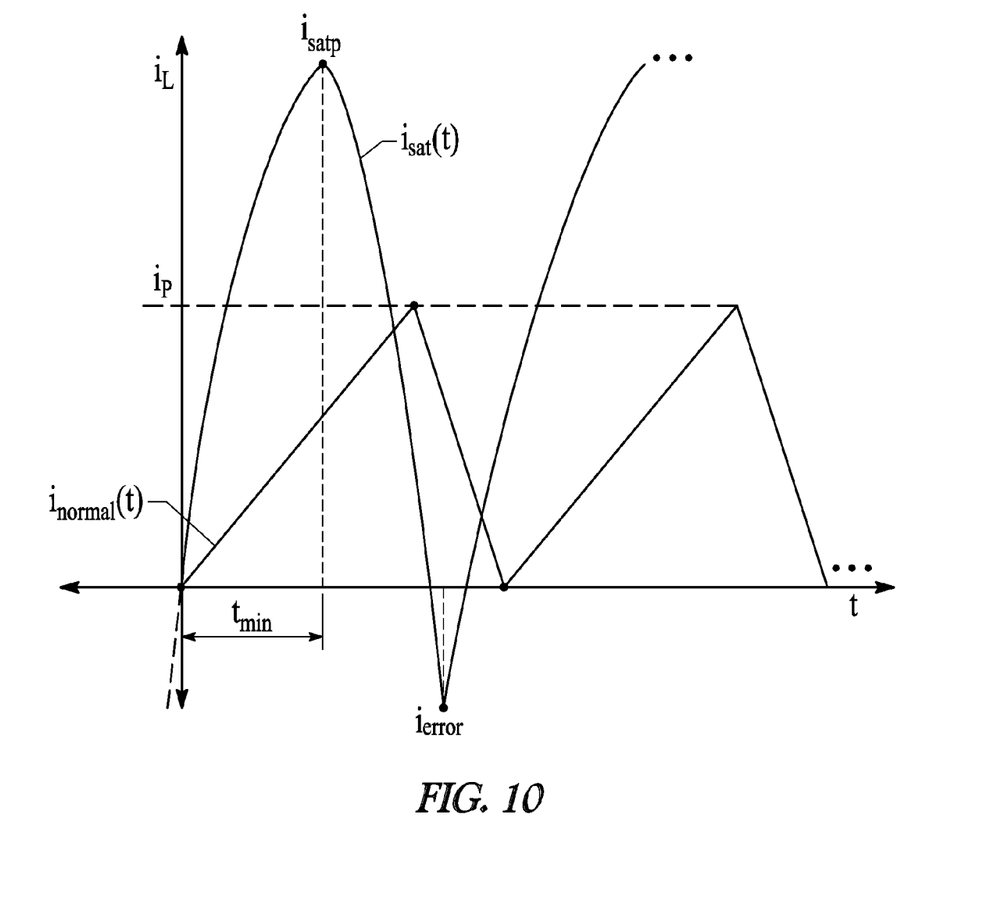
FIG. 10 illustrates plots of an example of an unsaturated inductor current, $i_{normal}(t)$, such as compared to a saturated inductor current, $i_{sat}(t)$, such as including a specified minimum duration of a charge phase.

FIG. 10 illustrates plots of an example of an unsaturated inductor current, $i_{normal}(t)$ as compared to a saturated inductor current, $i_{sat}(t)$, such as including a specified minimum duration of a charge phase (e.g., fill phase), $t_{min}$, such as for one or more of the inductive switching supply topologies such as shown in FIGS. 2-8.

In an example, if the reduction in inductance resulting from core saturation or other effects is large enough, a switching supply may fail to deliver adequate performance unless steps are taken to compensate for the temporary loss in inductance. For example, the switching supply may drain such significant current, such as from a battery, such as causing the battery voltage to temporarily or permanently decline to a value insufficient to sustain operation of the ambulatory or implantable medical device (e.g., falling below a "reset" threshold, triggering an end-of-device-life indicator, etc.). In an example, such as to deal with diminishing supply performance, the device can be configured to alter the operation of switching supply, such as by increasing inductor peak current in a current-limited control mode, increasing pulse width in a clocked frequency modulation control mode, entering a power-saving mode in order to reduce the load, or by one or more other contingencies.

In an illustrative example, an implantable medical device can include one or more supplies, such as the buck-boost (e.g., inverting) supply of FIG. 8, and during normal operation, the supply can use a peak inductor current threshold of 12 mA when in a buck mode, and a peak inductor current threshold of 36 mA when in a boost mode. In this illustrative example, when inductor saturation is detected, the supply can use a peak inductor current threshold of 36 mA regardless of whether the supply is in buck or boost mode, such as to at least partially compensate for reduced inductance of the power storage inductor.

In an example, an ambulatory or implantable device can be configured to enter or revert to its normal operating mode (e.g., a first operating mode) when core saturation is no longer detected (e.g., using information from one or more magnetic field detectors such as the core saturation detector discussed above, a Hall effect sensor, a voltage sensor, or one or more other sensors configured to detect an intense magnetic field), such as after entering (e.g., manually or automatically) a conditional MRI mode. In an example, one or more criteria can be used, such as by the controller of FIG. 1, to select the IMD operating mode, such as including time delay from de-assertion of the core saturation detector or Hall sensor, subsidence or reduction of coupled noise induced by the field in one or cardiac electrical activity sensors, subsidence of mechanical vibration or acoustic noise induced in the IMD or coupled to the IMD, such as due to the MRI spatial gradient fields, or using one or more other criteria or sensors.

In the example of FIG. 10, and as discussed above in the examples of FIGS. 6-8, the saturated inductor current $i_{sat}(t)$ can reach the normal specified peak current $i_p$ much more rapidly than during unsaturated operation. In an example, one or more comparators, such as the comparator CMP3 as shown in FIGS. 6-8, can use biasing conditions to detect $i_{normal}(t)$ crossing the specified peak current threshold $i_p$, with a specified latency (e.g., such as specified to limit overshoot of the normal inductor current). However, the present inventors have recognized, among other things, that the latency between the saturated inductor current $i_{sat}(t)$ crossing the specified peak current threshold $i_p$, and the assertion of the PKIC signal can result in significant overshoot of the inductor current, such as to a peak current $i_{satp}$ well beyond the desired specified peak current $i_p$.

One approach to respond to comparator latency is to leave the bias conditions of the one or more comparators unchanged, and to limit the minimum charging phase duration, such as to a minimum duration $t_{min}$, such as 1 µs, as discussed above in the illustrative examples. For example, the peak current comparison can be ignored when the inductor current crosses the specified peak current threshold at a time before the minimum charging phase duration. However, this approach can have disadvantages. For instance, the peak inductor current $i_{satp}$ can be relatively uncontrolled. Moreover, if the voltage input to the switching supply has significant resistance (e.g., poor voltage regulation, such as exhibited by a battery nearing the end of its usable life), the peak current may be sufficient to cause substantial voltage droop of the voltage input. Such voltage droop can upset other supplies or circuitry, such as in included in the ambulatory or implantable medical device.

The one or more comparators used to detect zero inductor current can also have a latency between an actual zero-crossing by the saturated inductor current, $i_{sat}(t)$, and assertion of the ZIC signal. The present inventors have also recognized, among other things, that a delay in assertion of the ZIC signal (e.g., a delay in detecting a zero-crossing of the inductor current) can result in a significant negative saturated inductor current, $i_{error}$, such as during the dump phase of operation. Negative inductor current can be undesirable because the negative current effectively drains energy back out of the storage inductor without performing useful work (e.g., the current is not supplied to the load), eroding efficiency. Also, if significant current is drained back out of the inductor, the total energy delivered to the load per fill-dump cycle becomes even more limited, potentially preventing the supply from maintaining the output voltage within a specified range (e.g., the supply can fail to meet the energy demand of the load).

Figure 11:
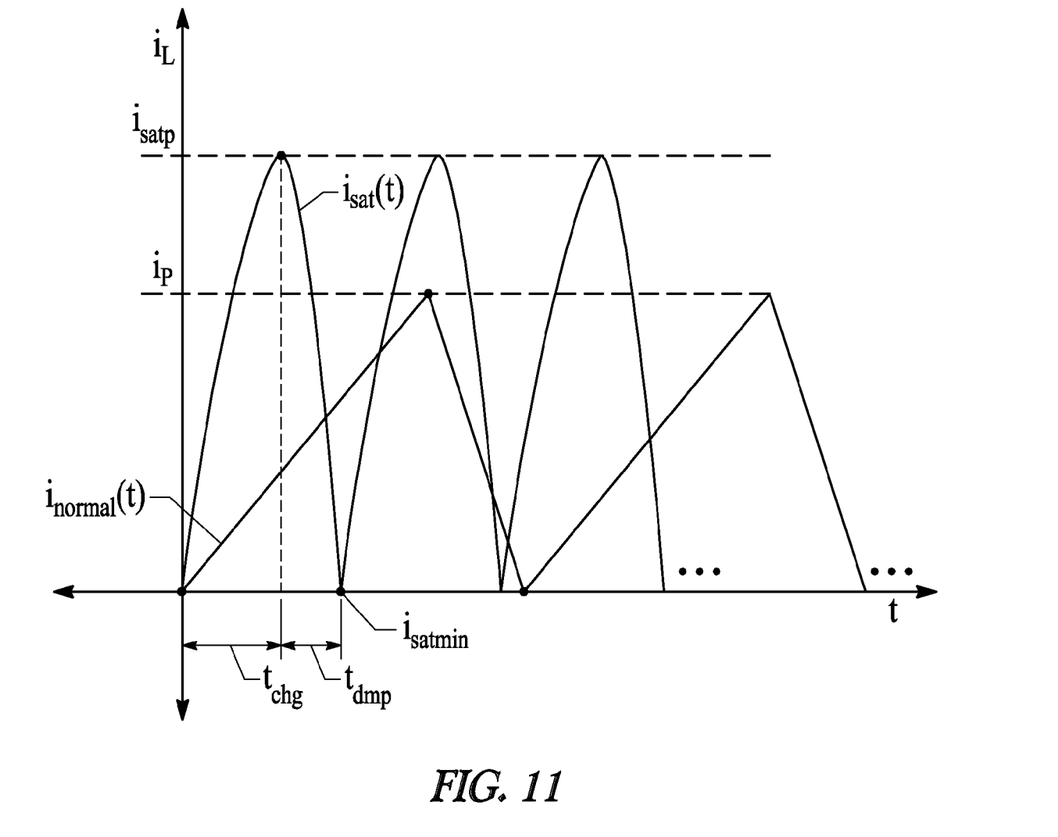
FIG. 11 illustrates plots of an example of an unsaturated inductor current, $i_{normal}(t)$, such as compared to a saturated inductor current, $i_{sat}(t)$, such as including one or more of specified charge phase or dump phase durations, or specified charge phase or dump phase current limits.

FIG. 11 illustrates plots of an example of an unsaturated inductor current $i_{normal}(t)$, as compared to a saturated inductor current, $i_{sat}(t)$, such as including one or more of a specified charge phase duration, $t_{chg}$, a specified dump phase durations, $t_{dmp}$, a specified charge phase saturated inductor current limit, $i_{satp}$, or a specified dump phase saturated inductor current limits, $i_{satmin}$.

In an example, one or more of the switching supplies of FIGS. 2-8 can be operated in a first mode during ambulatory operation, when an intense magnetic field is not present or detected, or when the device (e.g., device 100 of FIG. 1) is programmed to a non-MRI mode. Then, when the device is programmed to an MRI-mode, or such as when an intense magnetic field is detected, the one or more switching supplied of FIGS. 2-8 can be operated in a second mode, such as over the duration of exposure to the intense magnetic field. In an example, the one or more switching supplies of FIGS. 2-8 can be operated using the current-limited pulse frequency modulation control mode during normal ambulatory operation, and using the clocked pulse frequency modulation mode when exposed to the intense magnetic field. For example, the flip-flop FF1 of the examples of FIGS. 6-8 can be replaced or switched to operating as a D-type flip-flop, such as using a clocked data signal provided by the controller of FIG. 1, such as to provide synchronous charge and dump phases, such as triggered using information from a comparator such as CMP1, as shown in FIGS. 6-8. In an example, the supply can operate an a pulse-frequency modulation mode such as using one or more of the specified charge phase duration or the specified dump phase duration, $t_{chg}$, or $t_{dmp}$, respectively.

In an example, the supply can operate in a combination pulse-frequency or pulse-width modulation mode, such as by modifying one or more of the specified charge phase duration or the specified dump phase duration, $t_{chg}$, or $t_{dmp}$, respectively, but while still limiting the maximum dump-phase duration, such as to avoid negative inductor current. For example, if an error signal indicates significant output voltage error, one or more of the $t_{chg}$, or $t_{dmp}$ intervals can be extended, up to their respective specified maximum values. Then, in this example, a pulse repetition rate can be increased (providing more charge-dump cycles per unit time), such as to maintain output voltage to a constant load.

In an example, the supply can operate in a current-limited control mode, such as using one or more modified biasing conditions for one or more of the peak current detection circuit, or the zero current detection circuit. For example, one or more of CMP2 or CMP3, such as shown in FIGS. 6-8 can include at least two controllable bias conditions, such as provided by a first bias circuit or a second bias circuit. In a first bias condition, such as using the first bias circuit, the one or more comparators can be configured for current detection when the inductor current is similar to $i_{normal}(t)$ (e.g., when the inductor is unsaturated or has a normal inductance). The first bias condition can be used in the normal or ambulatory mode of operation (e.g., the first mode), such as to provide reduced comparator power consumption, as compared to a second bias condition. In an example, the second bias condition, such as using the second bias circuit, can include bias parameters or circuitry for higher-speed comparator operation (e.g. the second mode), such as when the one or more comparators are used for current detection when the inductor current is similar to $i_{sat}(t)$. For example, the higher-speed comparator operation can be used when the ambulatory or implantable medical device is exposed to an intense magnetic field, such as manually configured to the second mode, or automatically configured to the second mode (e.g., using a magnetic field detector such as a core saturation detector, a Hall effect sensor, or the like). In an example, the second bias condition can cause the one or more comparators to consume more power in the second mode than in the first mode. However, the overall battery life (e.g., longevity) of the ambulatory or implantable medical device need not be significantly reduced since the second mode of operation is used only temporarily, such as during exposure to an intense magnetic field.

In an example, the latency of the one or more comparators can be reduced, such as to limit one or more of peak or minimum inductor current overshoot, such as using the second bias condition, and thus the supply can terminate a charge phase (e.g., a fill phase) when the saturated inductor current reaches a specified peak current, $i_{satp}$, or the supply can terminate a dump phase when the saturated inductor current reaches a specified minimum inductor current, $i_{satmin}$, such as around or slightly above zero current.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device, comprising:
a magnetic field detector;
an inductive switching supply including:
an inductor including a ferromagnetic core;
a peak current comparator configured to compare an inductor current through the inductor to a specified peak current threshold; and
a zero current comparator configured to compare the inductor current to a specified minimum inductor current threshold;
a controller circuit configured to control a state of a switch using information from the peak current comparator and the zero current comparator when the implantable medical device is configured in a first mode of operation;
wherein the switch is configured to controllably charge the inductor; and
wherein the controller circuit is configured to adjust the implantable medical device to the first mode of operation in response to information provided by the magnetic field detector indicating an absence of an intense magnetic field.

2. The implantable medical device of claim 1, wherein the magnetic field detector includes a Hall effect sensor.

3. The implantable medical device of claim 1, wherein the magnetic field detector includes a core saturation detector configured to detect saturation of the inductor; and
wherein the intense magnetic field, when present, is intense enough to saturate the inductor.

4. The implantable medical device of claim 1, wherein the controller circuit is configured to adjust the implantable medical device to a second mode of operation in response to information provided by the magnetic field detector indicating a presence of the intense magnetic field.

5. The implantable medical device of claim 4, wherein the controller circuit includes at least one timer circuit;
wherein the controller circuit is configured to control the state of the switch using at least one of a specified maximum charge phase duration, or a specified maximum dump phase duration, using the timer circuit, when the implantable medical device is configured in the second mode of operation.

6. The implantable medical device of claim 5, wherein, in the second mode of operation, one or more of the specified maximum charge duration or the specified maximum dump phase duration is shorter than a corresponding charge phase duration or dump phase duration in the first mode operation.

7. The implantable medical device of claim 5, comprising:
an error comparator configured to compare an output of the inductive switching supply to a specified output reference, and configured to provide an error signal indicative of the comparison; and wherein the controller circuit is configured to adjust one or more of the charge phase duration, or the dump phase duration, using information about the error signal, when the implantable medical device is configured in the second mode of operation.

8. The implantable medical device of claim 5, comprising:
an error comparator configured to compare an output of the inductive switching supply to a specified output reference, and configured to provide an error signal indicative of the comparison; and
wherein the controller circuit is configured to adjust a repetition rate of successive charge and dump phases using information about the error signal, when the implantable medical device is configured in the second mode of operation.

9. The implantable medical device of claim 4, wherein the controller circuit is configured to adjust the implantable medical device back to the first mode of operation using information about the magnetic field provided by the magnetic field detector when the magnetic field detector is no longer exposed to an intense magnetic field.

10. The implantable medical device of claim 9, wherein at least one of the peak current comparator or the zero current comparator includes a first bias circuit used when the implantable medical device is in the first mode of a operation, and a second bias circuit used when the implantable medical device is in a second mode of operation; and
wherein the second bias circuit is configured to reduce a latency of at least one of the peak current comparator or the zero current comparator in the second mode of operation, as compared to the first mode of operation.

11. An implantable medical device, comprising:
a magnetic field detector;
an inductive switching supply including:
an inductor including a ferromagnetic core;
a peak current comparator configured to compare an inductor current through the inductor to a specified peak current threshold; and
a zero current comparator configured to compare the inductor current to a specified minimum inductor current threshold;
a controller circuit configured to control a state of a switch using information from the peak current comparator and the zero current comparator when the implantable medical device is configured in a first mode of operation;
wherein the switch is configured to controllably charge the inductor;
wherein at least one of the peak current comparator or the zero current comparator includes a first bias circuit used when the implantable medical device is in the first mode of a operation, and a second bias circuit used when the implantable medical device is in the second mode of operation;
wherein the second bias circuit is configured to reduce a latency of at least one of the peak current comparator or the zero current comparator in the second mode of operation, as compared to the first mode of operation; and
wherein the controller circuit is configured to adjust the implantable medical device to the second mode of operation using information about a magnetic field provided by the magnetic field detector when the magnetic field detector is exposed to an intense magnetic field.

12. A method, comprising:
detecting a magnetic field using an implantable medical device, the implantable medical device including an inductive switching supply;
in response to detecting the magnetic field, adjusting the implantable medical device to a first mode of operation when information about a detected magnetic field indicates an absence of an intense magnetic field; and
controllably charging an inductor included as a portion of the inductive switching supply via controlling a state of a switch, in the first mode of operation, the controlling the state of the switch including using information provided by:
comparing an inductor current to a specified peak current threshold; and
comparing the inductor current to a specified minimum inductor current threshold.

13. The method of claim 12, wherein the detecting the magnetic field includes detecting saturation of the inductor; and
wherein the intense magnetic field, when present, is intense enough to saturate the inductor.

14. The method of claim 12, comprising adjusting the implantable medical device to a second mode of operation when information about the detected magnetic field indicates a presence of an intense magnetic field.

15. The method of claim 14, comprising controlling the state of the switch, in the second mode of operation, using at least one of a specified maximum charge phase duration, or a specified maximum dump phase duration.

16. The method of claim 15, wherein, in the second mode of operation, one or more of the specified maximum charge duration or the specified maximum dump phase duration is shorter than a corresponding charge phase duration or dump phase duration in the first mode operation.

17. The method of claim 15, wherein the controlling the state of the switch, in the second mode of operation, includes:
comparing an output of the inductive switching supply to a specified output reference to provide an error signal indicative of the comparison; and
in response, adjusting one or more of the charge phase duration, or the dump phase during using information about the error signal.

18. The method of claim 15, wherein the controlling the state of the switch, in the second mode of operation, includes:
comparing an output of the inductive switching supply to a specified output reference to provide an error signal indicative of the comparison; and
in response, adjusting a repetition rate of successive charge and dump phases using information about the error signal.

19. The method of claim 14, comprising adjusting the implantable medical device back to the first mode of operation when information about the detected magnetic field indicates the implantable medical device is no longer exposed to an intense magnetic field.

20. The method of claim 14, wherein at least one of the comparing an inductor current to a specified peak current threshold or the comparing the inductor current to a specified minimum inductor current threshold includes using a first bias circuit when the implantable medical device is in the first mode of operation, and using a second bias circuit when the implantable medical device is in a second mode of operation; and
wherein the second bias circuit is configured to reduce a latency of the comparing, in the second mode of operation, as compared to the first mode of operation.

* * * * *